US011780756B2

United States Patent
Black et al.

(10) Patent No.: US 11,780,756 B2
(45) Date of Patent: Oct. 10, 2023

(54) INTEGRATED UNICELLULAR/FILAMENTOUS ALGAL PRODUCTION, HARVESTING AND REMEDIATION SYSTEM

(71) Applicant: Board of Regents of the University of Nebraska, Lincoln, NE (US)

(72) Inventors: Paul N. Black, Lincoln, NE (US); James W. Allen, Lincoln, NE (US); Timothy J. Nicodemus, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 756 days.

(21) Appl. No.: 16/653,696

(22) Filed: Oct. 15, 2019

(65) Prior Publication Data

US 2020/0148568 A1  May 14, 2020

Related U.S. Application Data

(60) Provisional application No. 62/746,371, filed on Oct. 16, 2018.

(51) Int. Cl.
*C02F 3/32* (2023.01)
*C02F 1/30* (2023.01)
(Continued)

(52) U.S. Cl.
CPC .............. *C02F 3/322* (2013.01); *C02F 1/30* (2013.01); *C02F 3/04* (2013.01); *C12M 25/02* (2013.01);
(Continued)

(58) Field of Classification Search
CPC .... C02F 3/322; C02F 1/30; C02F 3/04; C02F 3/10; C02F 2101/163; C02F 2103/06;
(Continued)

(56) References Cited

U.S. PATENT DOCUMENTS 6,465,240 B1 * 10/2002 Wexler .................. C02F 3/34
210/603
7,905,930 B2   3/2011 Oyler
(Continued)

FOREIGN PATENT DOCUMENTS

WO   WO 2008/156819 A2 * 12/2008
WO      2010006228 A2    1/2010

OTHER PUBLICATIONS

Chlorella, Wikipedia, Oct. 1, 2018, 1 page.
(Continued)

*Primary Examiner* — Fred Prince
(74) *Attorney, Agent, or Firm* — Suiter Swantz pc llo

(57) ABSTRACT

A method of removing nitrogen-bound nitrate from at least one of groundwater, surface water, or waste water is disclosed. The method includes providing contaminant-containing water from groundwater, surface water, and/or waste water sources. The method further includes adding the contaminant-containing water to an algal photobioreactor system. The method further includes adding an alga culture to the alga photobioreactor system. The method further includes adjusting temperature, $CO_2$ concentration, pH, light wavelength, and/or light intensity in the algal photobioreactor system to optimize the growth of the algae. The method further includes separating the algae from the water and harvesting algal biomass.

17 Claims, 12 Drawing Sheets

(51) Int. Cl.
| | |
|---|---|
| C02F 3/04 | (2023.01) |
| C02F 3/10 | (2023.01) |
| C12M 1/34 | (2006.01) |
| C12M 1/00 | (2006.01) |
| C12M 1/12 | (2006.01) |
| C02F 101/16 | (2006.01) |
| C02F 103/06 | (2006.01) |

(52) U.S. Cl.
CPC ............ *C12M 41/06* (2013.01); *C12M 41/12* (2013.01); *C12M 41/26* (2013.01); *C12M 41/30* (2013.01); *C12M 47/02* (2013.01); *C02F 3/10* (2013.01); *C02F 2101/163* (2013.01); *C02F 2103/06* (2013.01); *C02F 2209/02* (2013.01); *C02F 2209/06* (2013.01); *C12M 21/02* (2013.01); *Y02W 10/10* (2015.05); *Y02W 10/37* (2015.05)

(58) Field of Classification Search
CPC . C02F 2209/02; C02F 2209/06; C12M 25/02; C12M 41/06; C12M 41/12; C12M 41/26; C12M 41/30; C12M 47/02; C12M 21/02; Y02W 10/10; Y02W 10/37
USPC .............................. 435/257.1, 946; 210/602
See application file for complete search history.

(56) References Cited

U.S. PATENT DOCUMENTS

| | | | |
|---|---|---|---|
| 10,087,496 | B2 | 10/2018 | Hayakawa et al. |
| 2009/0324799 | A1 | 12/2009 | Hartman et al. |
| 2015/0337255 | A1 | 11/2015 | Kurata et al. |
| 2017/0321184 | A1 | 11/2017 | Hazlebeck et al. |

OTHER PUBLICATIONS

Cyanobacteria, Wikipedia, Jan. 7, 2016, 16 pages.
Gerardo et al., "Harvesting of microalgae within a biofinery approach: A review of the developments and case studies from pilot-plants", Algal Research 11 (2015) 248-262, Jul. 14, 2015,15 pages.
International Search Report and Written Opinion dated Feb. 25, 2020 for PCT/US2019/056495.
Allen, James et al., "Integration of biology, ecology and engineering for sustainable algal-based biofuel and bioproduct biorefinery", Bioresources and Bioprocessing, (2018) 5:47, https://dio.org/10.1186/s40643-018-0233-5, pp. 1-28.
Allen, James W. et al., "Induction of oil accumulation by heat stress is metabolically distinct from N stress in the green microalgae *Coccomyxa subellipsoidea* C169", Plos One, https://doi.org/10.1371/journal.pone.0204505, Sep. 27, 2018, pp. 1-20.
Allen, James W. et al., "Carbon and Acyl Chain Flux during Stress-induced Triglyceride Accumulation by Stable Isotopic Labeling of the Polar Microalga *Coccomyxa subellipsoidea* C169*", Journal of Biological Chemistry, vol. 292, No. 1, Jan. 6, 2017, pp. 361-375.
Allen, James W. et al., "Triacylglycerol synthesis during nitrogen stress involves the prokaryotic lipid synthesis pathway and acyl chain remodeling in the microalgae *Coccomyxa subellipsoidea*", Elsevier, Algal Research 10 (2015) 110-120, http://dx.doi.org/10/1016/j.algal.2015.04.019.
Allen, James W. et al., "Triglyceride quantification by catalytic saturation and LC-MS/MS reveals an evolutionary divergence in regioisometry among green microalgae", Elsevier, Algal Research 5 (2014) 23-31, http://dx.doi.org/10.1016/j.algal.2014.04.003.
Barros, Ana I. et al., "Harvesting techniques applied to microalgae: A review", Renewable and Sustainable Energy Reviews 41 (2015) 1489-1500, http://dx.doi.org/10.1016/j.rser.2014.09.037.
Christenson, Logan et al., "Production and harvesting of microalgae for wastewater treatment, biofuels, and bioproducts". Biotechnology Advances 29 (2011) 686-702, www.elsevier.com/locate/biotechadv.

\* cited by examiner

INTEGRATED UNICELLULAR/FILAMENTOUS ALGAL PRODUCTION, HARVESTING AND REMEDIATION SYSTEM

CROSS-REFERENCE TO RELATED APPLICATIONS

The present application claims the benefit under 35 U.S.C. § 119(e) of U.S. Provisional Application Ser. No. 62/746,371, filed Oct. 16, 2018, which is hereby incorporated by reference in its entirety.

TECHNICAL FIELD

The disclosure generally relates to filtration systems, and particularly to filtration of water through treatment by living organisms.

BACKGROUND

Treatment of contaminated water by biological entities (e.g., bacteria, algae, and fungi) is an emerging technology in wastewater, groundwater, and surface water treatment systems. These biological entities accumulate contaminants, often metabolizing them and incorporating the metabolized compounds into cellular components (e.g., proteins, nucleic acids and lipids). Algae is commonly proposed as the organism in bioremediation systems. Algae is photosynthetic and can survive in minimal media conditions while accumulating contaminants (e.g., nitrogenous and phosphorous compounds).

Algal water-remediation systems are hampered by several issues that limit large scale and commercial use of these systems. Algal remediation systems may require considerable staffing for monitoring the system and controlling the conditions for algal growth. Specifically, algal harvesting systems linked to remediation often require considerable energy inputs (e.g., centrifugation to remove the algae). The production of algal biomass, a potential source of income to offset operational costs, has yet to be optimized. One component of algal biomass and source for income, triglycerides (TAG), naturally accumulate in most green algae in response to abiotic stress, which is accompanied by reduced or slowed growth and reduced biomass. As such, there is a desire for a system and method for algal harvesting that provides for these efficiency and commercial viability issues.

SUMMARY

A filtration assembly is disclosed, in accordance with one or more embodiments of the present disclosure. In one embodiment, the filtration assembly includes a filter plate. In another embodiment, the filter plate contains at least one pore. In another embodiment, the filtration assembly further includes a filter column. In another embodiment, the filter column is attached to an algal photobioreactor system and configured to receive at least one species of unicellular alga grown in the algal photobioreactor system. In another embodiment, the filter assembly further includes a least one species of filamentous alga disposed within the filter column.

An algal photobioreactor system is disclosed, in accordance with one or more embodiments of the present disclosure. In one embodiment, the algal photobioreactor system includes a photobioreactor chamber. In another embodiment, the algal photobioreactor system further includes a filtration assembly. In another embodiment, the algal photobioreactor system may further include a unicellular alga. In another embodiment, the algal photobioreactor system further includes a light source.

A method of removing nitrogen-bound nitrate from at least one of groundwater, surface water, or waste water is disclosed, in accordance with one or more embodiments of the present disclosure. In one embodiment, the method includes the step of providing contaminant-containing water from groundwater, surface water, and/or waste water sources. In another embodiment, the method may further include the step of adding the contaminant-containing water to an algal photobioreactor system. In another embodiment, the method may further include the step of adding an alga culture to the alga photobioreactor system. In another embodiment, the method may further include the step of adjusting temperature, $CO_2$ concentration, pH, light wavelength, and/or light intensity in the algal photobioreactor system to enhance the growth of the algae. In another embodiment, the method may further include separating the algae from the water. In another embodiment, the method may further include harvesting algal biomass.

An algal biomass with high lipid content prepared by a process is disclosed, in accordance with one or more embodiments of the present disclosure. In one embodiment, the process includes providing water from a groundwater, surface water, and/or waste water source. In another embodiment, the process may further include adding the water to an algal photobioreactor system. In another embodiment, the process may further include adjusting at least one of temperature, $CO_2$ concentration, pH, light wavelength, or light intensity in the algal photobioreactor system to enhance triglyceride production. In another embodiment, the process may further include separating the algae from the water. In another embodiment, the process may further include harvesting the algal biomass.

DETAILED DESCRIPTION OF THE INVENTION

The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

FIGS. 1A through 9 generally illustrate a system and method for water remediation through an algal photobioreactor, in accordance with one or more embodiments of the present disclosure.

Embodiments of the present disclosure are directed to an algal photobioreactor system. More particularly, embodiments of the present disclosure are directed to an algal photobioreactor system implementing a filamentous alga as a biofilter, which is capable of removing non-filamentous algae from water following decontamination of the water of various contaminants by the non-filamentous algae.

Embodiments of the present disclosure provide an integrated system that improves growth and harvesting of microalgae using an enclosed algal photobioreactor that can be scaled and deployed for nitrate remediation coincident with oil synthesis for biofuel and/or bioproduct development. The present disclosure provides: [1] high algal growth and oil synthesis (e.g., through the microalgae such as *Coccomyxa subellipsoidea* or *Tetradesmus obliquus*) using municipal waste water or ground water by optimizing enclosed photobioreactor conditions including temperature, wavelength and intensity of light and $CO_2$ concentration; and [2] a novel microalgae harvesting system using a filtration assembly prepared from the filamentous algae (e.g., such as *Bumilleriopsis filiformis* or *Tribonema aequale*). These optimized, or at least improved, conditions are supported by studies using high-resolution mass spectrometry demonstrating metabolic flux of carbon from $CO_2$ to define fatty acid biosynthetic and lipid metabolic networks culminating in high levels of oil synthesis. Advantageously, the algal photobioreactor system of the present disclosure provides: an integrated system that combines algae cultivation and the use of algal biomass for biofuel and/or bioproduct using the components of waste water or ground water treatment; a system wherein triglycerides (TAG) can be produced in high amounts and recovered for conversion to other useful bioproducts and used in alternative processes; and a system wherein algal biomass growth and growth rate can be maximized such that the biomass can be grown, recovered and converted to other useful products and used in other processes.

Figure 1A:
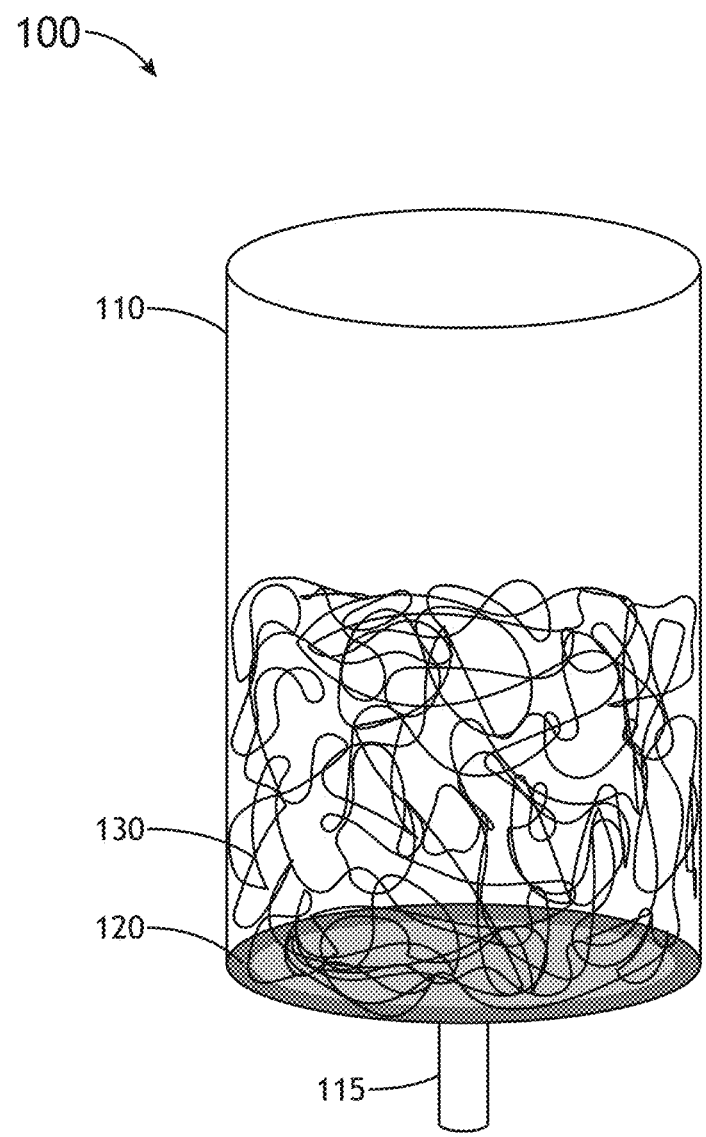
FIG. 1A is a conceptual view of a filtration assembly prior to the filtration of water containing unicellular algae, in accordance with one or more embodiments of this disclosure.
Figure 1B:
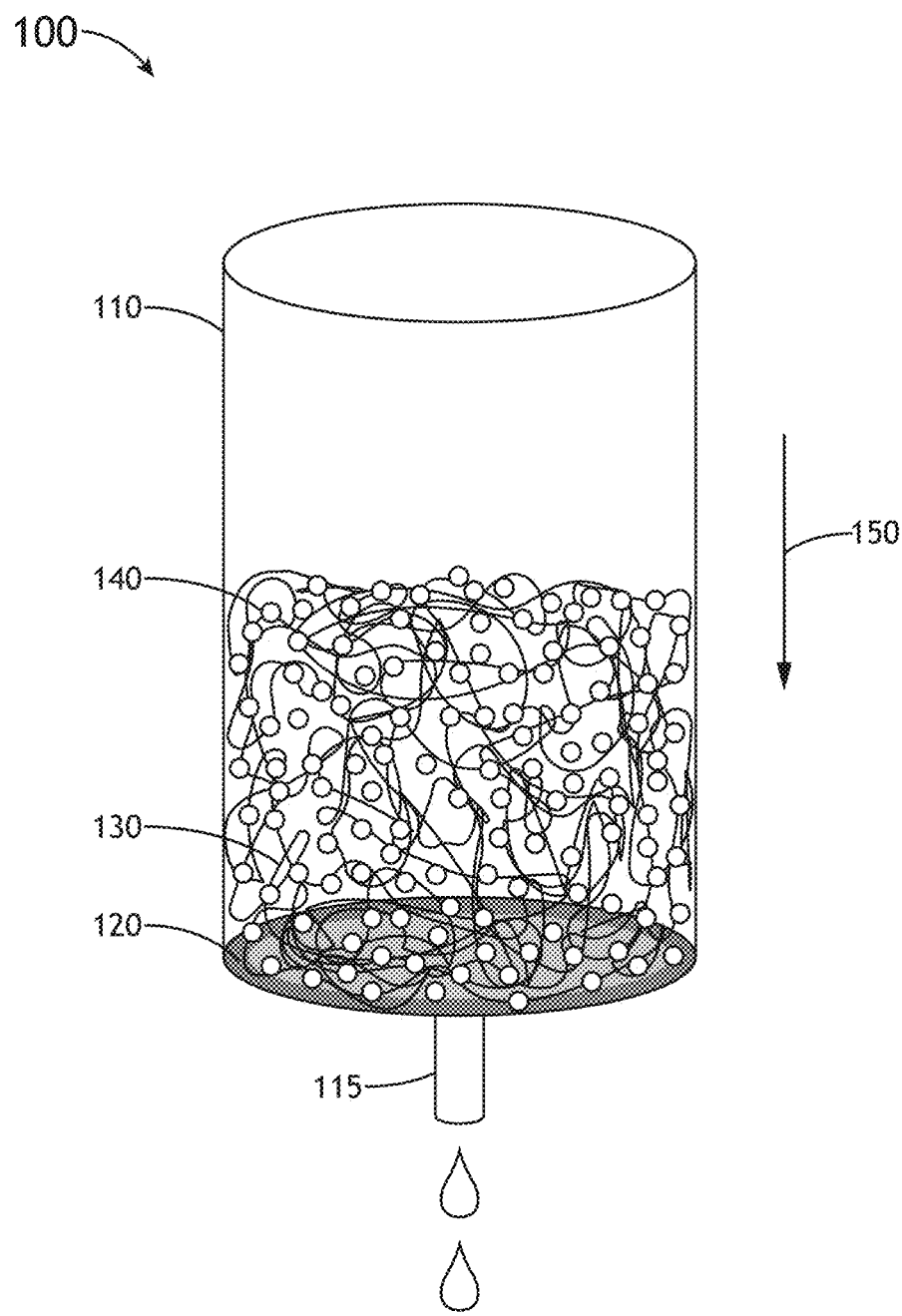
FIG. 1B is a conceptual view of the filtration assembly during the filtration of water containing unicellular algae, in accordance with one or more embodiments of this disclosure.
Figure 1C:
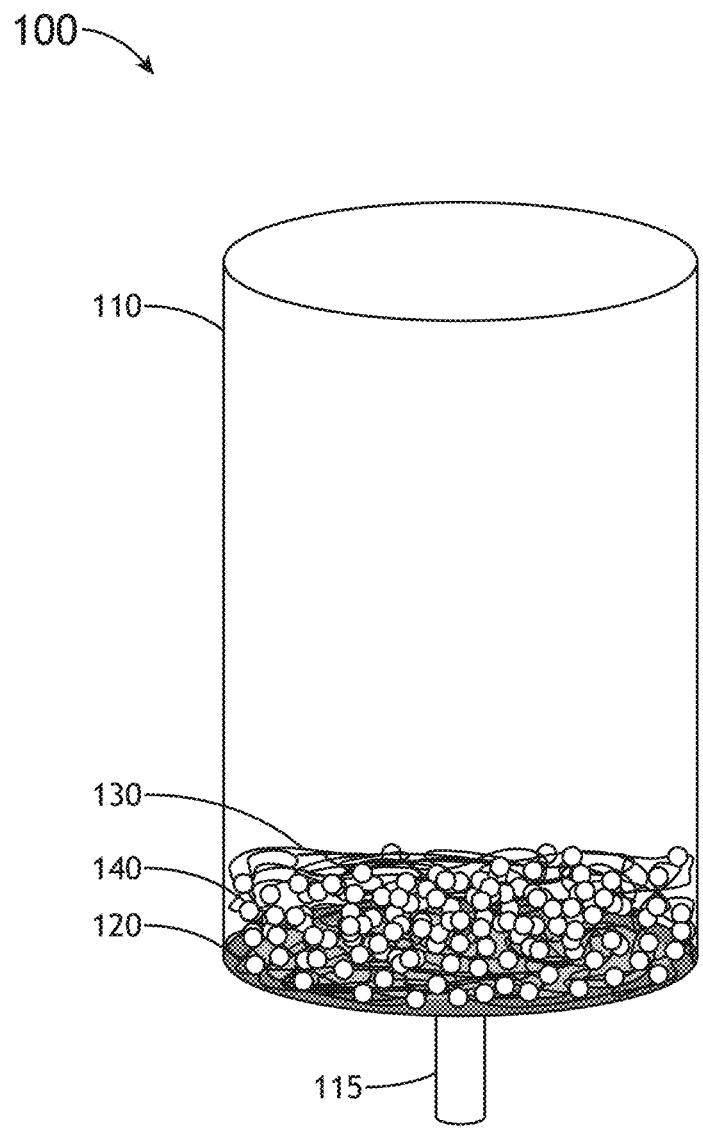
FIG. 1C is a conceptual view of the filtration assembly after the filtration of water containing unicellular algae, in accordance with one or more embodiments of this disclosure.

FIGS. 1A-1C illustrate a filtration assembly 100, in accordance with one or more embodiments of this disclosure. FIG. 1A illustrates the filtration assembly 100 prior to filtration of the water.

In one embodiment, the filtration assembly 100 includes a filter column 110. The filter column 110 provides support for the components of the filtration assembly 100 and is configured to allow water to flow through the components of the filtration assembly 100.

The volume of the filter column 110 may be any volume of filter column 110 used in filtration assemblies 100. For example, the filter column 110 may have a volume of 20 ml. In another example, the filter column 110 may a volume of 20 L. In still another example, the filter column 110 may have a volume of 2000 L or greater. The volume may be of any size required to fulfill the need of the filtration system (e.g., a filtration system for a large city may need filter columns 110 considerably larger than 2000 L). In one embodiment, the filter column includes an output port 115.

The filter column 110 may be formed from any material known in the art. For example, the filter column 110 may be formed from polymer, resin, stainless steel, silicon, plastic, or other similar material, and any combination thereof.

In another embodiment, the filtration assembly includes a filter plate 120 (e.g., a frit). The filter plate 120 supports the stationary phase (e.g., the filter material of the filter column 110), preventing the stationary phase from flowing through the filter column 110. The filter plate 120 contains one or more pores that allow water to pass through the column.

The filter plate 120 may be formed of any material known in the art suitable for making filter plates. For example, the filter may be, but is not required to be, formed from stainless steel, polymer, resin, metal, plastic, silicon, or other similar material, and any combination thereof. In one embodiment, the filter plate 120 is made from stainless steel.

The filter plate 120 may be used multiple times. For example, the filter plate 120 is used at least 2 times, at least 3 times, at least 4 times, at least 5 times, at least 6 times, at least 7 times, at least 8 times, at least 9 times, or at least 10 times or more without decreasing efficacy of the filtration assembly 100. In one embodiment, the filter plate 120 includes one or more pores within the surface of the plate. The pores are configured to have a diameter ranging from 0.25 µm to 5 µm, where values such as 0.25 µm, 0.30 µm, 0.35 µm, 0.40 µm, 0.45 µm, 0.50 µm, 0.55 µm, 0.60 µm, 0.65 µm, 0.70 µm, 0.75 µm, 0.80 µm, 0.85 µm, 0.90 µm, 0.95 µm, 1 µm, 1.05 µm, 1.10 µm, 1.15 µm, 1.20 µm, 1.25 µm, 1.30 µm, 1.35 µm, 1.40 µm, 1.45 µm, 1.50 µm, 1.75 µm, 2 µm, 2.5 µm, 3 µm, 3.5 µm, 4 µm, 4.5 µm, and 5 µm are envisioned. For instance, the filter plate 120 may have pores that are about 1 µm in diameter.

The filter plate 120 may take on any shape known in the art. For example, the filter plate 120 may be shaped as a disk. By way of another example, the filter plate 120 may be shaped to conform to the dimensions of the filter column 110

In another embodiment, the filtration assembly 100 includes filamentous algae 130 as the stationary phase of the filter column 110. The filamentous algae binds and/or traps unicellular algae, cellular debris, and other components of the material to be filtered, allowing the filtrate to exit through the filter plate 120, and out of the filter column 110.

In one embodiment, the filamentous algae 130 is grown onto the filter plate 120 over time, eventually becoming sizable enough to act as a stationary phase for the filter column 110. In another embodiment, the filamentous alga is added directly to the filter column 110, where the filamentous algae 130 form a stationary phase through the gravity. In yet another embodiment, the filamentous algae 130 is added directly to the filter column 110, where the filamentous algae forms a stationary phase as water flows through the filter column 110 and out the output port 115.

The filamentous algae 130 may include any algae known in the art that forms a structure of long chains, threads, filaments or pseudofilaments. These structures may interact and bind with other unicellular algae through electrostatic processes, trap unicellular algae within the matrix formed by the filamentous algae 130, and/or otherwise bind unicellular algae through other processes. The species of filamentous algae 130 may be any species of filamentous algae 130 known in the art including, but not limited to, *Bumilleriopsis filiformis, Tribonema aequale, Tribonema affine, Tribonema minus*, and *Tribonema viride*. The filamentous algae 130 may contain more than one filamentous algae species. It should be noted that newly discovered algal species, or algal species with newly discovered properties for binding unicellular algae may be used in the filtration assembly 100. Therefore, the above description should not be interpreted as a limitation of the present disclosure, but merely as an illustration.

FIG. 1B is a diagram illustrating a filtration assembly 100 during the filtration of water containing algae, in accordance with one or more embodiments of this disclosure.

In another embodiment, the filtration assembly 100 further includes unicellular algae 140. The unicellular algae 140 may uptake a variety of compounds (e.g., nitrates and phosphates) from the aqueous environment, ultimately reducing the concentration of these components in the water. For example, the unicellular algae 140 may remove nitrogen-bound nitrate from water contaminated with nitrogen-bound nitrate. After decontamination of the water, the unicellular algae 140 may be configured to bind to the filamentous algae 130 (e.g., as in FIG. 1B) where the unicellular algae 140 may be later removed and harvested.

The species of unicellular algae 140 used in the filtration assembly 100 may include any species of unicellular algae 140 capable of uptaking nitrogenous and/or phosphorous compounds. For example, the unicellular algae 140 may include, but is not limited to, *Coccomyxa subellipsoidea* or *Tetradesmus obliquus*.

The unicellular algae 140 may also include species capable of producing relatively high concentrations of triglycerides (TAG). TAG can be extracted from the algae and converted into an oil that can be used for a variety of purposes (e.g., fuel, plastics). The production of a high TAG-producing algae may provide a non-fossil fuel source of oil and an income stream that may alleviate a portion of the costs of water bioremediation. TAG naturally accumulates in most green algae in response to abiotic stresses, which is accompanied by reduced or slowed growth and reduced biomass. Strains of unicellular algae 140 that optimize TAG production concurrent with uptake of contaminants may be used. For example, the unicellular alga *Coccomyxa subellipsoidea* may be used within the filtration assembly 100. Alternatively, the unicellular alga *Tetradesmus obliquus* may be used within the filtration assembly 100. It should be noted that newly discovered algal species, or algal species with newly discovered properties for contaminant uptake and/or TAG production may be used in the filtration assembly 100. Therefore, the above description should not be interpreted as a limitation of the present disclosure, but merely as an illustration.

FIG. 10 is a diagram illustrating a filtration assembly 100 after the filtration of water containing unicellular algae 140, in accordance with one or more embodiments of this disclosure. After the water has passed though the filter column 110, the column 110 retains an algal biomass containing a mix of filamentous algae 130 and unicellular algae 140. In one embodiment, another amount of water containing unicellular algae 140 may be run through the filter column 110. In another embodiment, the algal mass is removed from the filter. Removal of the algal biomass from the filter column 110 may be performed by any method known in the art. For example, the algal biomass may be poured out of the filter column 110. In another example, the algal biomass may be aspirated out of the filter column 110.

In one embodiment, the filamentous algae 130 disposed in the filter column 110 is reused for sequential water purification cycles. For example, the filamentous algae 130 may remain in the filter column 110 for multiple purification cycles, aggregating more and more unicellular algae 140. In another example, the filamentous algae 130 and the unicellular algae 140 are separated from each other after removal of the algal biomass from the filter column 110, and a portion of the filamentous algae 130 isolated from the algal biomass is reused. In embodiments, the filamentous algae 130 may be reused at least once, at least 2 times, at least 3 times, at least 4 times, at least 5 times, at least 6 times, at least 7 times, at least 8 times, at least 9 times, or at least 10 times or more.

In one embodiment, a portion of the recovered algae containing filamentous algae 130 and/or non-filamentous unicellular algae 140 is used to restart the algal culture. In another embodiment, a newly propagated algal culture containing filamentous algae 130 and/or non-filamentous unicellular algae 140 is used to restart the algal culture.

Figure 2:
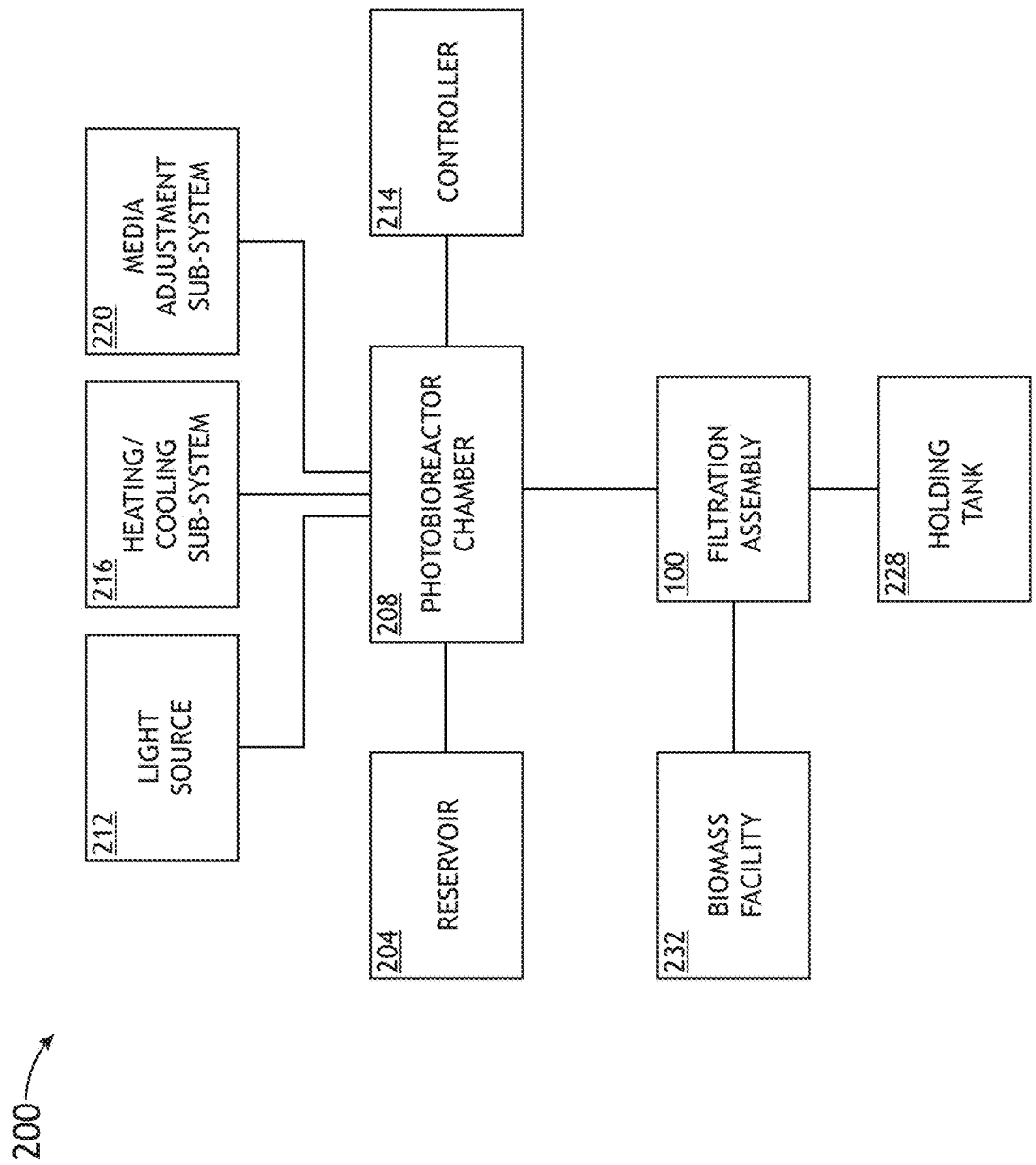
FIG. 2 is a block diagram of an algal photobioreactor system, in accordance with one or more embodiments of this disclosure.

FIG. 2 illustrates a block diagram view of an algal photobioreactor system 200, in accordance with one or more embodiments of the present disclosure. The algal photobioreactor system 200 is configured to grow algae in the presence of light to remove contaminants (e.g., nitrogen-bound nitrates and/or phosphates) from groundwater, surface water, and/or waste water (e.g., from municipal facilities and/or industrial facilities). The algal photobioreactor system 200 may be configured to harvest algae. Components of the harvested algae (e.g., TAG, proteins, carbohydrates, etc.) may be extracted and/or converted for industrial and/or commercial use.

In one embodiment, the algal photobioreactor system 200 may include a reservoir 204. The reservoir holds the contaminated water prior to use by the algal photobioreactor system 200. The reservoir 204 may include any container known in the art to hold water. For example, the reservoir 204 may include a tank. In another example, the reservoir may include a pool. The reservoir 204 may take on any shape or size. The reservoir may also be a naturally or artificially formed depression or cavity in the ground. For example, the reservoir 204 may include a pond. In an alternative embodiment, the algal photobioreactor system 200 does not include a reservoir 204. Rather, the algal photobioreactor system 200 may be connected directly to a municipal or industrial water supply.

In another embodiment, the algal photobioreactor system 200 includes a photobioreactor chamber 208. The photobioreactor chamber 208 may be configured to provide a volumetric space for algal growth in the contaminated water. The photobioreactor chamber 208 may be further configured to expose the algae to light.

The photobioreactor chamber 208 may take on any shape capable of supporting an algal culture. For example, the photobioreactor chamber 208 may have a cylindrical shape (e.g., a tube). In another example, the photobioreactor chamber 208 may have cuboid shape. In still another example, the photobioreactor chamber 208 may have an ovoid shape (e.g., a tube with an oval cross-section)

The photobioreactor chamber 208 may be configured to be of any size capable of supporting an algal photoreactor system 200. For example, the photobioreactor chamber 208 may have a volume greater than 10 L. In another example, the photobioreactor chamber 208 may have a volume greater than 10,000 L.

The photobioreactor chamber 208 may be formed of any material capable of storing water and allowing the water to be exposed to light. For example, the photobioreactor chamber 208 made be constructed of glass (e.g., borosilicate, soda-lime silicate, or quartz). In another example, the photobiotic chamber 208 may be constructed of plastic (e.g., polypropylene, polycarbonate, high-density polyethylene (HDPE), low-density polyethylene (LDPE), or co-polyester). In still another example, the photobiotic chamber 208 may be constructed of recycled materials (e.g., plastic water bottles).

In another embodiment, the algal photobioreactor system 200 includes the filtration assembly 100. The filtration assembly 100 separates the water from the algae after the algae has reduced the concentration of contaminants from the water. After the filtration assembly 100 has separated the algae the water, the filtration assembly 100 retains an algal biomass within the filter column 110. The algal biomass may then may then be removed from the filter column 110 (e.g., by pouring or aspirating).

In another embodiment, the algal photobioreactor system 200 includes a light source 212. The light source 212 provides light needed by the photosynthetic algae for growth. In one embodiment, the light source 212 includes a natural light source (e.g., the Sun). In another embodiment, the light source includes an artificial light source (e.g., incandescent, halogen, fluorescent, or light emitting diode (LED)). In another embodiment, the algal photobioreactor system 200 utilizes both natural and artificial light. For example, the algal photobioreactor system 200 may turn on artificial light during the night or when days are cloudy.

The light source 212 may be configured to generate light of a selected one or more wavelengths. For example, the light source 212 may be configured to emitting any combination of infrared, visible, or ultraviolet light. For example, the light source 212 includes a broadband light source configured to emit light having a wavelength or wavelength range between 400-700 nm. For instance, in the case of a broadband light source, the light source 212 is configured to emit light having a wavelength with ranges as follows: 400-500 nm, 400-600 nm, 500-700 nm, or 600-700 nm. In another example, the light source 212 includes a red light source configured to emit light having a wavelength or wavelength range between 622-780 nm. For instance, in the case of a red light source 212, the red light source 212 is configured to emit light having a wavelength with ranges or values as follows: 622-700 nm, 622-725 nm, 650-700 nm, 650-750 nm, 650-780 nm, 622 nm, 625 nm, 630 nm, 640 nm, 650 nm, 660 nm, 670 nm, 675 nm, 680 nm, 690 nm, 700 nm, 710 nm, 720 nm, 730 nm, 740 nm, 750 nm, 760 nm, 770 nm, or 780 nm. In another example, the light source 212 includes a green light source configured to emit light having a wavelength or wavelength range between 520-610 nm. For instance, in the case of a green light source 212, the green light source 212 is configured to emit light having a wavelength with ranges or values as follows: 520-580 nm, 520-600 nm, 520-550 nm, 550-600 nm, 550-610 nm, 520 nm, 525 nm, 530 nm, 540 nm, 550 nm, 560 nm, 570 nm, 575 nm, 580 nm, 590 nm, 600 nm, 605 nm, or 610 nm. In another example, the light source 212 includes a blue light source configured to emit light having a wavelength or wavelength range between 450-520 nm. For instance, in the case of a blue light source 212, the blue light source 212 is configured to emit light having a wavelength with ranges or values as follows: 400-450 nm, 450-480 nm, 450-470 nm, 460-495 nm, 470-495 nm, 400 nm, 425 nm, 450 nm, 455 nm, 460 nm, 465 nm, 470 nm, 475 nm, 480 nm, 485 nm, 490 nm, 495 nm, or 500 nm. The intensity of the light is preferably about 100-800 µmol/m$^2$/sec, with ranges and values such as 100-300 µmol/m$^2$/sec, 100-400 µmol/m$^2$/sec, 100-500 µmol/m$^2$/sec, 100-600 µmol/m$^2$/sec, 100-700 µmol/m$^2$/sec, 200-400 µmol/m$^2$/sec, 200-600 µmol/m$^2$/sec, 200-700 µmol/m$^2$/sec, 300-500 µmol/m$^2$/sec, 300-600 µmol/m$^2$/sec, 300-700 µmol/m$^2$/sec, 300-800 µmol/m$^2$/sec, 400-500 µmol/m$^2$/sec, 400-600 µmol/m$^2$/sec, 400-700 µmol/m$^2$/sec, 400-800 µmol/m$^2$/sec, 500-600 µmol/m$^2$/sec, 500-700 µmol/m$^2$/sec, 500-800 µmol/m$^2$/sec, 100 µmol/m$^2$/sec, 200 µmol/m$^2$/sec, 300 µmol/m$^2$/sec, 400 µmol/m$^2$/sec, 500 µmol/m$^2$/sec, 600 µmol/m$^2$/sec, 700 µmol/m$^2$/sec, and 800 µmol/m$^2$/sec are envisioned.

In another embodiment, the algal photobioreactor system 200 includes a holding tank 228. The holding tank captures the water that leaves the filtration assembly 100. The holding tank 228 may be type of container known in the art to hold water. For example, the holding tank 228 may be a cistern. In another example, the holding tank 228 may be a pool. The holding tank 228 may be of any shape or size. The holding tank 228 may also be a naturally or artificially formed depression of cavity in the ground. For example, the holding tank 228 may be a pond. In another embodiment, the algal photobioreactor system 200 does not have a holding tank 228 (e.g., the algal photobioreactor system 200 is connected directly to a municipal or industrial water system.)

In another embodiment, the algal photobioreactor system 200 includes a biomass facility 232. The biomass facility 232 is configured to store the algal biomass produced by the algal photobioreactor system 200. The biomass facility 232 may be further configured to process the algal biomass. For example, the biomass facility 232 may be configured to dewater the biomass. In another example, the biomass facility 232 may be configured to extract components from the biomass (e.g., TAG, proteins, and/or carbohydrates). The biomass facility 232 may also be configured to perform quality control tests on the biomass (e.g., to determine TAG percentage, proteins percentage, and/or carbohydrate percentage).

In another embodiment, the algal photobioreactor system 200 includes one or more pumps. The pumps may be configured to move liquid components of the algal photobioreactor system 200 (e.g., water, media adjusting components) from one component of the algal photobioreactor system 200 to another. The pumps may also be configured to circulate water (e.g., within the photoreactor chamber). The pumps may be of any type of liquid pump known in the art including, but not limited to, dynamic pumps (e.g., centrifugal or submersible pumps) and/or positive displacement pumps (e.g., diaphragm, gear, peristaltic, lobe, and/or piston pumps).

In another embodiment, the algal photobioreactor system 200 includes one or more valves. The valves may be configured to restrict flow of fluid through the algal photobioreactor system 200 when the valves are closed, and to allow the flow of fluid through the algal photobioreactor system 200 when the valves are opened. The valves may be of any type of valve known in the art including, but not limited to, gate valves, globe valves, check valves, plug valves, ball valves, pinch valves, and/or pressure relief valves. In another embodiment, all valves, or a portion of the valves, are operated manually. In another embodiment, all valves, or a portion of the valves, are operated automatically.

In another embodiment, the algal photobioreactor system 200 further includes one or more sensors. The sensors may be configured to detect and/or measure specific characteristics of the algal photobioreactor system 200. For example, sensors may be configured to measure the temperature, pH, water pressure, and carbon dioxide levels within the photobioreactor chamber 208. Sensors may also detect conditions outside of the photobioreactor chamber, including but not limited to, light levels, temperature, and humidity. Other parameters not listed here may also be detect or measure by sensors, therefore the above description should not be interpreted as a limitation of the present disclosure, but merely an illustration.

In another embodiment, the algal photobioreactor system 200 includes one or more controllers 248. The one or more controllers 248 may include one or more processors and memory. The one or more processors may be configured to carry out one or more steps described in the present disclosure.

The one or more controllers 248 may be coupled (e.g., physically and/or communicatively coupled) to the one or more pumps, valves, sensors, and/or other components of the algal photobioreactor system 200. For example, one or more signals may be transmitted and/or received between a controller 214 and one or more sensors located within the photobioreactor chamber 208.

In another embodiment, the algal photobioreactor system 200 includes a heating/cooling sub-system 216. The heating/cooling sub-system 216 is configured to maintain the photoreactor chamber 208 at a selected temperature. The selected temperature of the photoreactor chamber 208 is typically within a range of about 25-36° C., where ranges and values such as 25-30° C., 30-36° C., 33-34° C., 25° C., 27° C., 29° C., 30° C., 31° C., 32° C., 33° C., 34° C., 35° C. and 36° C. are envisioned.

In one embodiment, the heating/cooling sub-system 216 includes one or more devices (e.g., one or more actuators) to open and close doors and/or windows in the structure that houses the photoreactor chamber 208 (e.g., a ceiling window in a greenhouse). The heating/cooling sub-system 216 may further include heaters, coolers (e.g., air-conditioning units), fans and/or other devices to control the temperature of the photoreactor chamber 208. The algal photobioreactor system 200 may also use low-energy technology (e.g., green technology) to heat and/or cool the photoreactor chamber 208. For example, geothermal technology (e.g., Provencal wells, or rock heat boxes) and/or solar panels may be used to control temperature. The heating/cooling sub-system 216 may be communicatively coupled to the controller 214. For example, one or more signals may be sent and/or received between a controller 214 and a heater of the heating/cooling sub-system 216 to adjust the temperature of the photobioreactor chamber 208.

In another embodiment, the algal photobioreactor system 200 includes a media adjustment sub-system 220. The media adjustment sub-system 220 is configured to adjust the environmental conditions of the photoreactor chamber 208. For example, the media adjustment sub-system 220 may add components to the photobioreactor chamber that control or adjust the pH of the algal environment. In another example, the media adjustment sub-system 220 may add components to the photobioreactor chamber 208 to prevent the algal culture from being taken over by an unwanted biological entity. In another example, the media adjustment sub-system 220 may add filamentous algae 130 or unicellular algae 140 to start and/or maintain the algal culture. In one embodiment, the media adjustment sub-system 220 includes at least one valve, pump, or sensor. In another embodiment, the media adjustment sub-system 220 is communicatively coupled to the controller 214. For example, one or more signals may be sent and/or received between the controller 214 and a valve, pump, and/or sensor of the media adjustment sub-system 220 to release unicellular algae 140 into the photobioreactor chamber 208.

The media adjustment sub-system 220 may also add carbon dioxide to the photoreactor chamber 208. Algal cultures require carbon dioxide for growth. Addition of carbon dioxide to algal cultures also increases biomass production. In another embodiment, the media adjustment sub-system 220 is configured to adjust the carbon dioxide concentrations within the photoreactor chamber 208 to between 0.5% to 5.5%, where ranges and values such as 1-1.5%, 1-2%, 1-2.5%, 2-2.5%, 2-3%, 2-4%, 3-5%, 4-5%, 1%, 1.5%, 2%, 2.5%, 3%, 3.5%, 4%, 4.5%, and 5% are envisioned.

Figure 3:
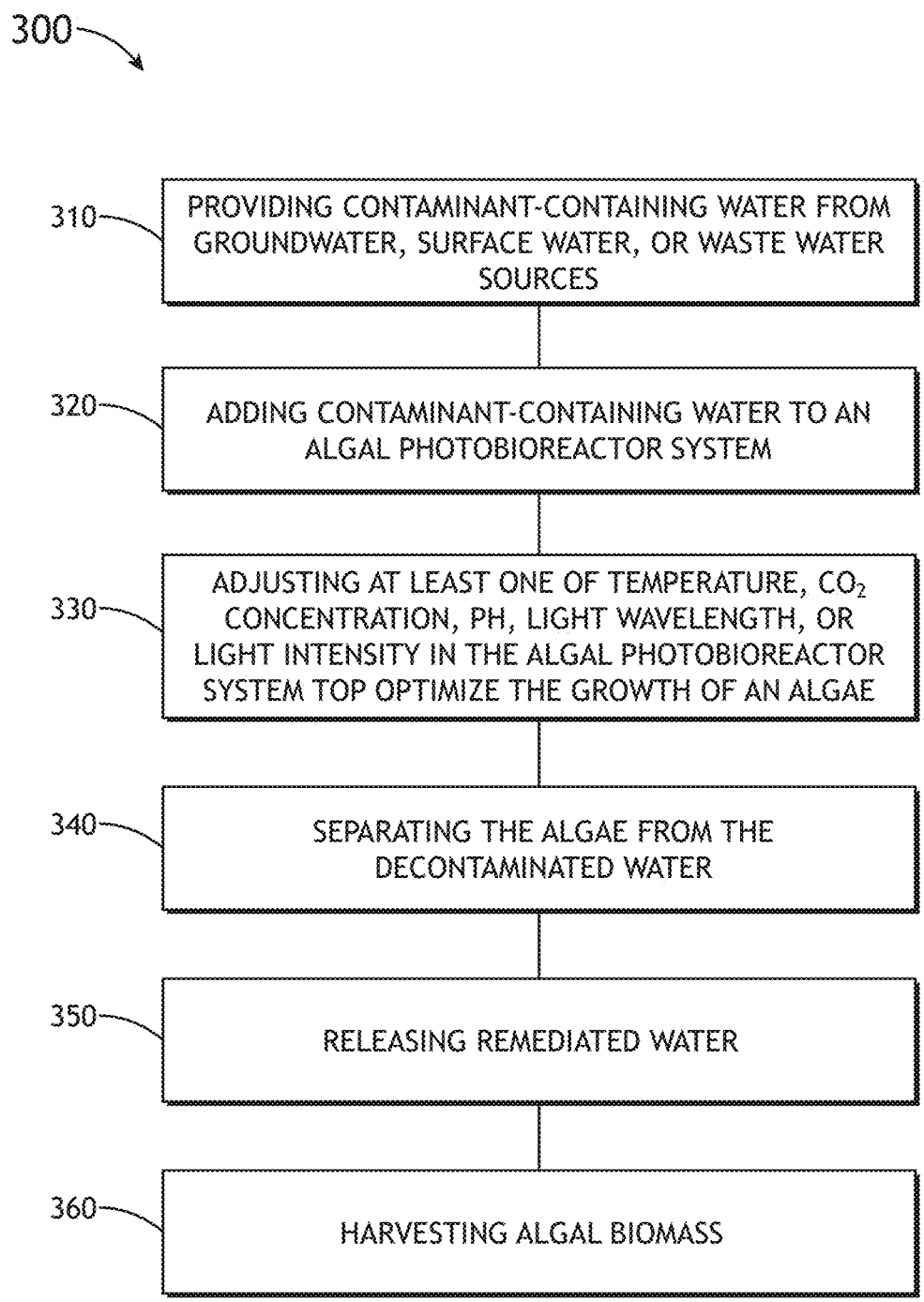
FIG. 3 is a process flow diagram illustrating a method of removing nitrogen-bound nitrate from at least one of ground water, surface water or waste water, in accordance with one or more embodiments of this disclosure.

FIG. 3 illustrates a method 300 for removing nitrogen-bound nitrate from waste water, surface water and/or groundwater, in accordance with one or more embodiments of the present disclosure.

In one embodiment, step 310 of method 300 includes providing contaminant-containing water from groundwater, surface water, or waste water sources. For example, groundwater from a nitrate-contaminated municipal well may be provided for nitrate removal. By way of another example, surface water from a nitrate-contaminated lake may be provided for nitrate removal. By way of another example, waste water from a livestock confinement complex may be provided for nitrate removal. The contaminated water may be stored in a reservoir 204 before processing.

In another embodiment, step 320 of method 300 includes adding contaminant-containing water to an algal photobioreactor system 200. The algal photobioreactor system 200 utilized in the method 300 may include the algal photobioreactor system 200 described previously herein. In another embodiment, the algal photobioreactor system utilized in the method 300 may include algal photobioreactor systems that use different water decontamination strategies (e.g., an external decontamination system (e.g., pond-based) or internal decontamination systems with different methods for algal separation).

In another embodiment, step 325 of the method includes adding an algal culture to the algal photobioreactor system 200. The algal culture may contain any type of algae known in the art to uptake contaminants (e.g., nitrogen-bound nitrate) from an aqueous environment. For example, the algal culture may contain *Coccomyxa subellipsoidea*. In another example, the algal culture may contain *Tetradesmus obliquus*. As described herein, it should be noted that newly discovered algal species, or algal species with newly discovered properties for contaminant uptake and/or TAG production may be used in the algal photobioreactor system.

Therefore, the above description should not be interpreted as a limitation of the present disclosure, but merely as an illustration.

In another embodiment, step 330 of the method includes adjusting at least one of temperature, $CO_2$ concentration, pH, wavelength, or light intensity in the algal photobioreactor system 200. The adjustment of one or more of these parameters may be controlled by a controller 214. In another embodiment, one or more of the parameters may be adjusted manually. For example, the temperature of the algal photobioreactor system 200 (e.g., particularly the photobioreactor chamber 208) may be adjusted by manually adjusting the heating/cooling sub-system 216. In another example, light intensity may be adjusted by manually turning on a light source 212. Adjustments may be made to the algal photobioreactor system at the beginning of the decontamination process (e.g., when the water and algae are first combined), at one or more times during the decontamination process, or continuously during the decontamination process.

In another embodiment, the filtration assembly 100 is used concurrently with the algal photobioreactor system 200. As described herein, an algal photobioreactor system 200 utilizing the filtration assembly 100 will use filamentous algae 130 as a component of the filtration assembly 100. For example, during harvest, the filamentous algae 130 acts as the stationary phase in the filter column 110 to bind unicellular algae 140.

In another embodiment, step 340 of the method 300 includes separating the algae from the decontaminated water (e.g., the water is separated from the algae once the contaminants have been lowered to a selected level.) For example, the water and algae may be separated after the measured concentration of nitrogen bound nitrate is less than 10 ppm. In another example, the water may be released after the measured concentration of nitrogen bound nitrate is less than 1 ppm. The selected level of nitrogen bound nitrogen bound nitrate may be determined by the operator of the algal photobioreactor system 200.

In another embodiment, the filtration assembly 100 of the algal photobioreactor system 200 removes at least 5% more, at least 10% more, at least 20% more, at least 30% more, at least 40% more, at least 50% more, at least 60% more at least 70% more, at least 80% more, at least 90% more or at least 100% more nitrogen-bound nitrate from waste water and ground water than other algal photobioreactor systems not utilizing the filtration assembly 100 of the present disclosure.

In another embodiment, step 350 of the method 300 includes releasing the remediated water. Once the water has been released by the algal photobioreactor system 200, the water may be released into a holding tank 228, where the water may await further processing and/or testing before being released into the environment (e.g., into a river or a municipal water system). The water may also be released directly into the environment (e.g., without a holding tank 228).

In another embodiment, step 360 of the method 300 includes harvesting the algal biomass. Once the algal biomass is separated from the decontaminated water and removed from the filtration assembly 100, the algal biomass may be taken to a biomass facility 232. The algal biomass may be dewatered further before the algal biomass is transferred to another facility for further processing. In another embodiment, the algal biomass is further processed at the biomass facility (e.g., extraction of lipids ((e.g., TAG), proteins, carbohydrates, etc.)). The biomass facility 232 may be further configured to test the algal biomass for various parameters (e.g., TAG concentration and/or protein concentration). In another embodiment, the algal biomass serves as the feedstock for biofuel and bio-based product production.

The method 300 of the algal photobioreactor system 200 and filtration assembly 100 provided by the present disclosure results in more algal biomass than known systems. In another embodiment, the algal biomass collected by the algal photobioreactor system 200 is at least 5% more, at least 10% more, at least 20% more, at least 30% more, at least 40% more, at least 50% more, at least 60% more, at least 70% more, at least 80% more, or at least 90% more biomass than previous algal photobioreactor systems to remove the same amount of nitrate from waste water or ground water.

In another embodiment the method 300 of the disclosure, oil (e.g., lipids, TAG, etc.) is produced in the unicellular algae and collected as water filters through the system. In another embodiment, the oil accumulates in the unicellular algae between 20-250 mg/L at a rate of 10-15 days, where oil accumulation values are envisioned to be 20 mg/L, 30 mg/L, 50 mg/L, 75 mg/L, 100 mg/L, 125 mg/L, 150 mg/L, 175 mg/L, 200 mg/L, 225 mg/L and 250 mg/L. Accumulation may be achieved in about 2-15 days, where ranges and values such as 1-2 days, 2-4 days, 4-6 days, 6-8 days, 8-10 days, 10-12 days, 10-14 days, 12-14 days, 12-15 days, 1 day, 2 days, 3 days, 4 days, 5 days, 6 days, 7 days, 8 days, 9 days, 10 days, 11 days, 12 days, 13 days, 14 days, and 15 days are envisioned. Optimally, oil accumulates in the unicellular algae 140 in the algal photobioreactor system 200 having a temperature range of about 25-36° C., where ranges and values such as 25-30° C., 30-36° C., 33-34° C., 25° C., 27° C., 29° C., 30° C., 31° C., 32° C., 33° C., 34° C., 35° C. and 36° C. are envisioned.

In another embodiment of the disclosure, the algal photobioreactor system 200 and the method 300 of the present disclosure harvests algae with enhanced oil (e.g., TAG-based oil) synthesis, when compared to previous algal photobioreactor systems. In another embodiment, the algal photobioreactor system 200 and method 300 of the present disclosure collects algae that produce at least 5% more oil, at least 10% more, at least 20% more, at least 30% more, at least 40% more, at least 50% more, at least 60% more at least 70% more, at least 80% more, at least 90% more or at least 100% more oil than algal photobioreactor systems not utilizing the algal photobioreactor system 200 and method 300 of the present disclosure. In one embodiment of this disclosure, the lipid content of the algal biomass ranges from 30% to 35% of a dry weight of the algal biomass. In another embodiment, the lipid content of the algal biomass ranges from 35% to 40% of a dry weight of the algal biomass.

In another embodiment of the present disclosure, the method 300 of removing nitrogen-bound nitrate using the algal photobioreactor system 200 and filtration assembly 100 removes at least 30% of nitrogen-bound nitrate from waste water or ground water, at least 40% of nitrogen-bound nitrate from waste water or ground water, at least 50% of nitrogen-bound nitrate from waste water or ground water, at least 60% of nitrogen-bound nitrate from waste water or ground water, at least 70% of nitrogen-bound nitrate from waste water or ground water, at least 80% of nitrogen-bound nitrate from waste water or ground water, at least 90% nitrogen-bound nitrate from waste water or ground water, or 100% nitrogen-bound nitrate from waste water or ground water.

Figure 4:
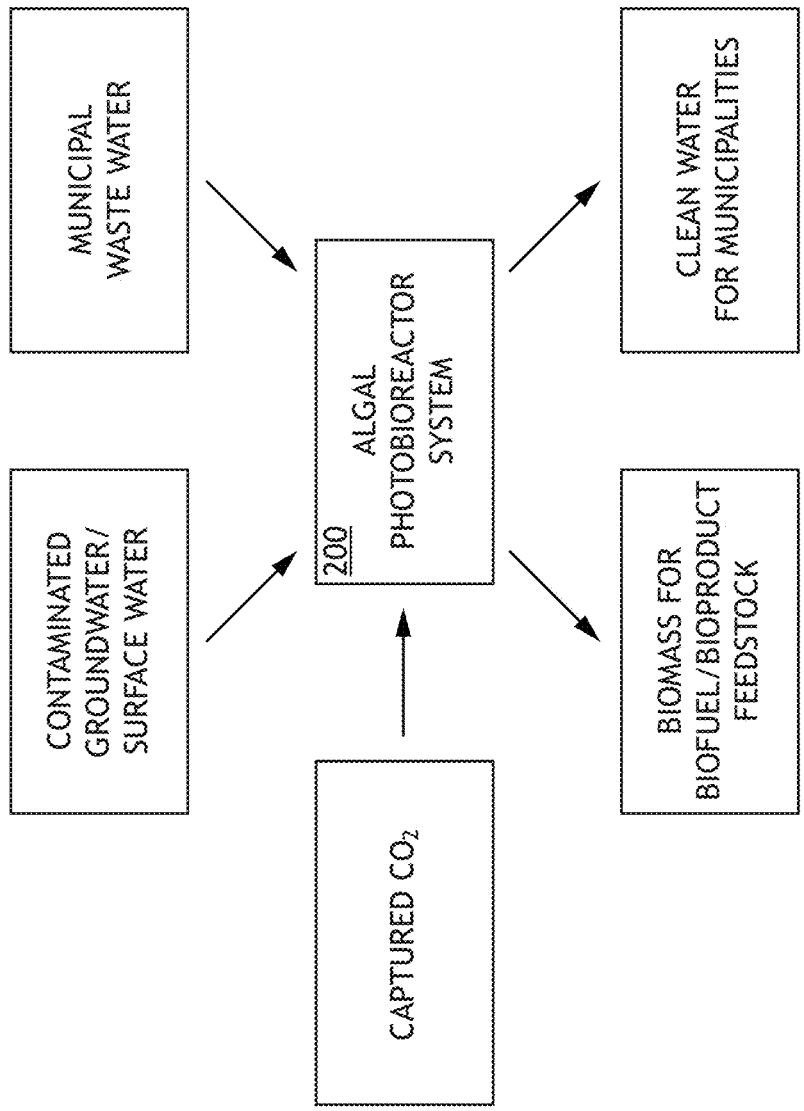
FIG. 4 is a block diagram illustrating an environment integrating water remediation and biomass production for biofuel and bio-based products using an algal photobioreactor system, in accordance with one or more embodiments of this disclosure.

FIG. 4 is an illustration that describes an environment integrating water remediation and biomass production for biofuel and bio-based products using the filtration assembly 100 and the algal photobioreactor system 200 of the present disclosure. The algal photobioreactor system 200 and method 300 may be incorporated into environments that have high levels of nitrogen-bound nitrate in ground water (e.g., from agricultural runoff). Contaminating nitrogen-bound nitrate may be removed using an algal photobioreactor system 200 to generate algal biomass. The algal biomass may be increased through addition of $CO_2$ into the algal photoreactor system 200 (e.g., sourced from power plants, ethanol plants, etc.). The resulting clean water provides municipal needs, which is substantially free of nitrogen-bound nitrate. Municipal waste water may treated through an integrated treatment system that includes an algal photoreactor system 200 resulting in downstream clean water that can also be recycled for municipal needs. In one embodiment, the algal biomass serves as a feedstock for biofuel and/or other bio-based products.

Figure 5:
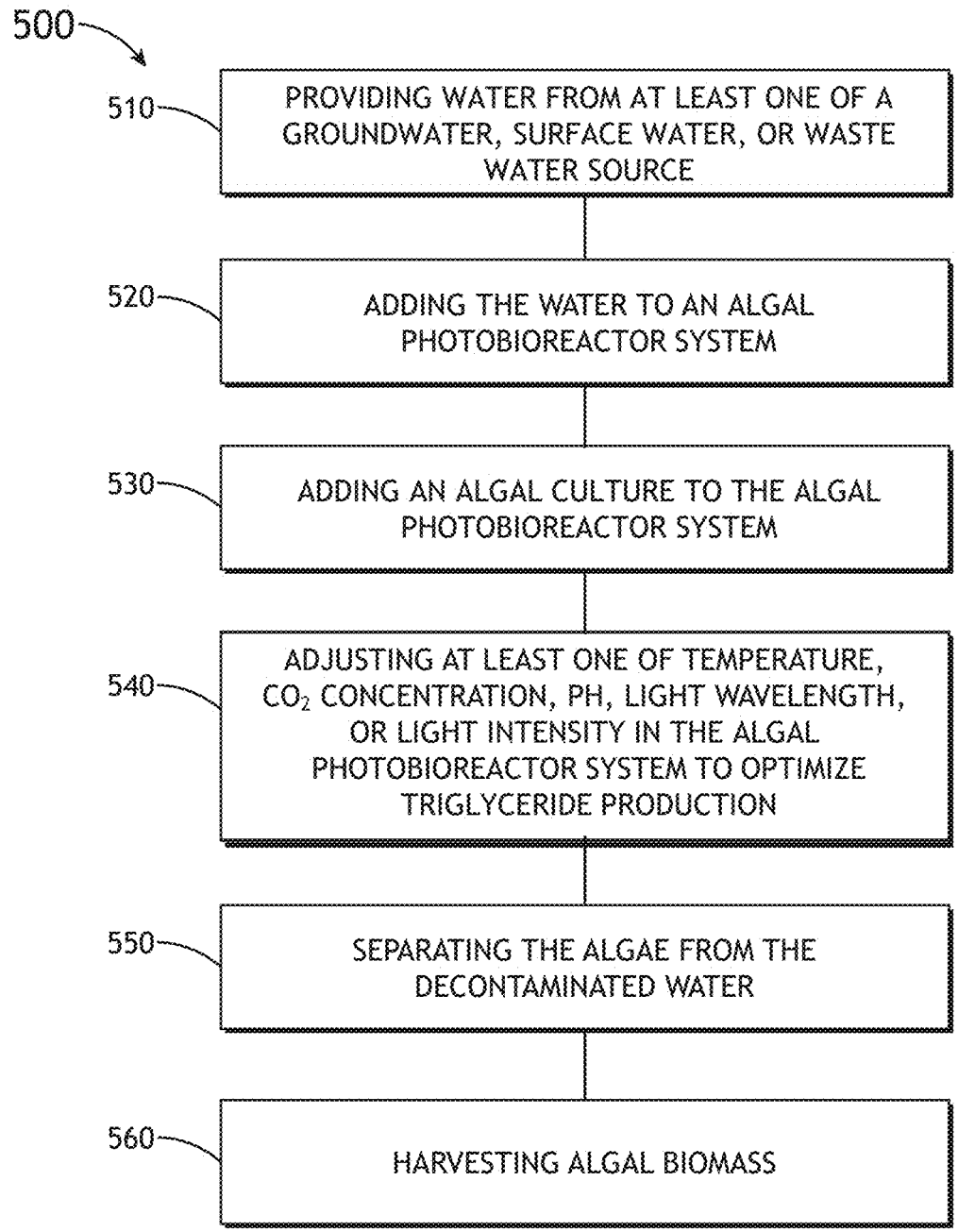
FIG. 5 is a process flow diagram illustrating a method of preparing an algal biomass with high lipid content, in accordance with one or more embodiments of this disclosure.

FIG. 5 is a process flow diagram illustrating a process 500 wherein an algal biomass with high lipid contact is prepared, in accordance with one or more embodiments of this disclosure. In one embodiment, the process includes the step 510 of providing water from at least one of a groundwater, surface water, or waste water source. In another embodiment, the process includes step 520 of adding the water to an algal photobioreactor system (e.g., the algal photobioreactor system 200 described herein.) In another embodiment, the process includes step 530 of adding an algal culture to the algal photobioreactor system. For example, the algal culture may contain one or more strains of algae known to produce high amounts of lipids (e.g., *Coccomyxa subellipsoidea* or *Tetradesmus obliquus*.). In another embodiment, the process includes step 540 of adjusting the temperature, $CO_2$ concentration, pH, light wavelength, and/or light intensity in the algal photobioreactor system to increase triglyceride production. For example, the $CO_2$ concentration may be raised from atmospheric $CO_2$ levels (e.g., ~0.04%) to 2.5%.

In another embodiment, the process includes step 550 of separating the algae from the water. The separation may be performed by the filter assembly 100. In another embodiment, the separation may be performed through other method (e.g., centrifugation). In one embodiment, the process includes step 660 of harvesting the algal biomass. The harvest may be performed by dewatering the column and pouring or rinsing out the filter column 110. In another embodiment, different methods of harvesting may be used (e.g., aspiration). In one embodiment of this disclosure, the lipid content of the algal biomass ranges from 10% to 35% of a dry weight of the algal biomass. In another embodiment, the lipid content of the algal biomass ranges from 10% to 20% of a dry weight of the algal biomass. In another embodiment, the lipid content of the algal biomass ranges from 20% to 30% of a dry weight of the algal biomass. In another embodiment, the lipid content of the algal biomass ranges from 30% to 35% of a dry weight of the algal biomass. In another embodiment, the lipid content of the algal biomass from 35% to 40% of a dry weight of the algal biomass.

EXAMPLE 1

Production and Utilization of a Filamentous Algal Filter Assembly

*Coccomyxa subellipsoidea* C169 was originally obtained from the Microbial Culture Collection, National Institute for Environmental Studies, Japan (NIES 2166). *Tetradesmus obliquus* was obtained from UTEX, University of Texas-Austin, USA (UTEX B72). Filamentous algae species *Tribonema aequale* obtained from the National Center for Marine Algae (Maine, USA; NCMA 2166) and *Bumilleriopsis filiformis* obtained from the Culture Collection of Autotrophic Organisms (Czech Republic; CCALA 224) were used as filtration media for the removal of unicellular green algae from growth media.

All of the algal species were maintained on agar plates prepared using Bold's Basal Medium under continuous white light. For growth, algae were transferred from the agar plate cultures to 20 mL of modified Bold's Basal Medium (BBM) and grown at 25° C. in an Innova 43 white-lighted shaking incubator (New Brunswick Scientific) set to 125 RPM for 1 week; the algae grown under these conditions were used as the inoculum for the larger cultures, including those in batch 1-6 L photobioreactors.

Photobioreactor growth of filamentous algae was photoautotrophic in 1 L photobioreactors using BBM with 500 µmols photons/$m^2$/sec provided by conventional 200 W equivalent CFM bulbs. A correlated gas flow meter (Cole-Parmer) was used to control aeration of compressed air or mixes with $CO_2$ (0.5 L $min^{-1}$) from the flask bottom, making the bottle a bubble lift batch photobioreactor. The filamentous algae (*T. aequale* or *B. fififormis*) were grown to stationary phase, or approximately 1 g dry weight algae per L media, which was obtained in 5-7 days of continuous growth.

For the filtering studies the unicellular microalgae *C. subelipsoidea* or *T. obliquus* was grown to stationary phase (OD ~3) in BBM cultures in 1-6 L batch photobioreactors under continuous white-light illumination in the presence of 1% $CO_2$. For conditions promoting enhanced oil synthesis, growth of *C. subelipsoidea* or *T. obliquus* was performed under limiting nitrogen-bound nitrate conditions.

For the preparation of the biofilters, the filamentous algae were grown as noted above and allowed to settle to the bottom of the growth vessels for several hours and excess water decanted to ~10% of the original volume. A 4 µm stainless steel filtration disk is placed at the bottom of a 20 mL capacity (can vary to increase volume) column is used to concentrate the filamentous algae from the slurry through gravity. The packed and dewatered column of filamentous algae is subsequently used as a biofilter to remove unicellular species (*C. subelfipsoidea* or *T. obliquus*) grown as detailed above; without the filamentous biofilters, the unicellular algae are not retained by the stainless-steel filtration disk.

EXAMPLE 2

Utilization of a Filamentous Algal Filter Assembly Coupled to an Algal Photobioreactor System A waste water or groundwater photobioreactor system growing *C. subellipsoidea* or *T. obliquus* is linked to a filtration system using a column packed with *B. fififormis* or *T. aequale*, having a disk-shaped stainless-steel plate at the bottom having a 1 µm pore size. Waste water with actively growing *C. subellipsoidea* or *T. obliquus* was run through both filters following the removal of nitrogen-bound nitrate.

The use of the *B. fififormis* and *T. aequale* biofilters eliminates the need to harvest cells by centrifugation and is more viable method that is cost effective. Using biofilters prepared on stainless-steel disks (0.10 mm thickness) with a 1 µm pore size from both species, the *B. fififormis* is much more efficient and takes only 8% the biomass when compared to the *T. aequale* biofilters. Using cultures of unicellular *C. subellipsoidea* or *S. dimorphus* at high density (>100 mg/L/day (dry weight)), the *B. fififormis* biofilter is 99% effective while the *T. aequale* biofilter is 93% effective in retaining biomass. We have shown that these biofilters can be reused up to 5 times with no loss in efficiency.

EXAMPLE 3

Optimization of Algal Growth and Lipid Production

Algal growth was optimized under defined and secondary wastewater growth conditions. We have completed studies establishing the optimal growth conditions of *C. subellipsoidea* and *T. obliquus* resulting in nitrogen-bound nitrate remediation coincident with enhanced TAG (e.g., oil) synthesis. these are biofuel/bioproduct production strains suitable for use in more temperate latitudes. Our analyses have been conducted in temperature-controlled 1-200 L photobioreactors.

Figure 6:
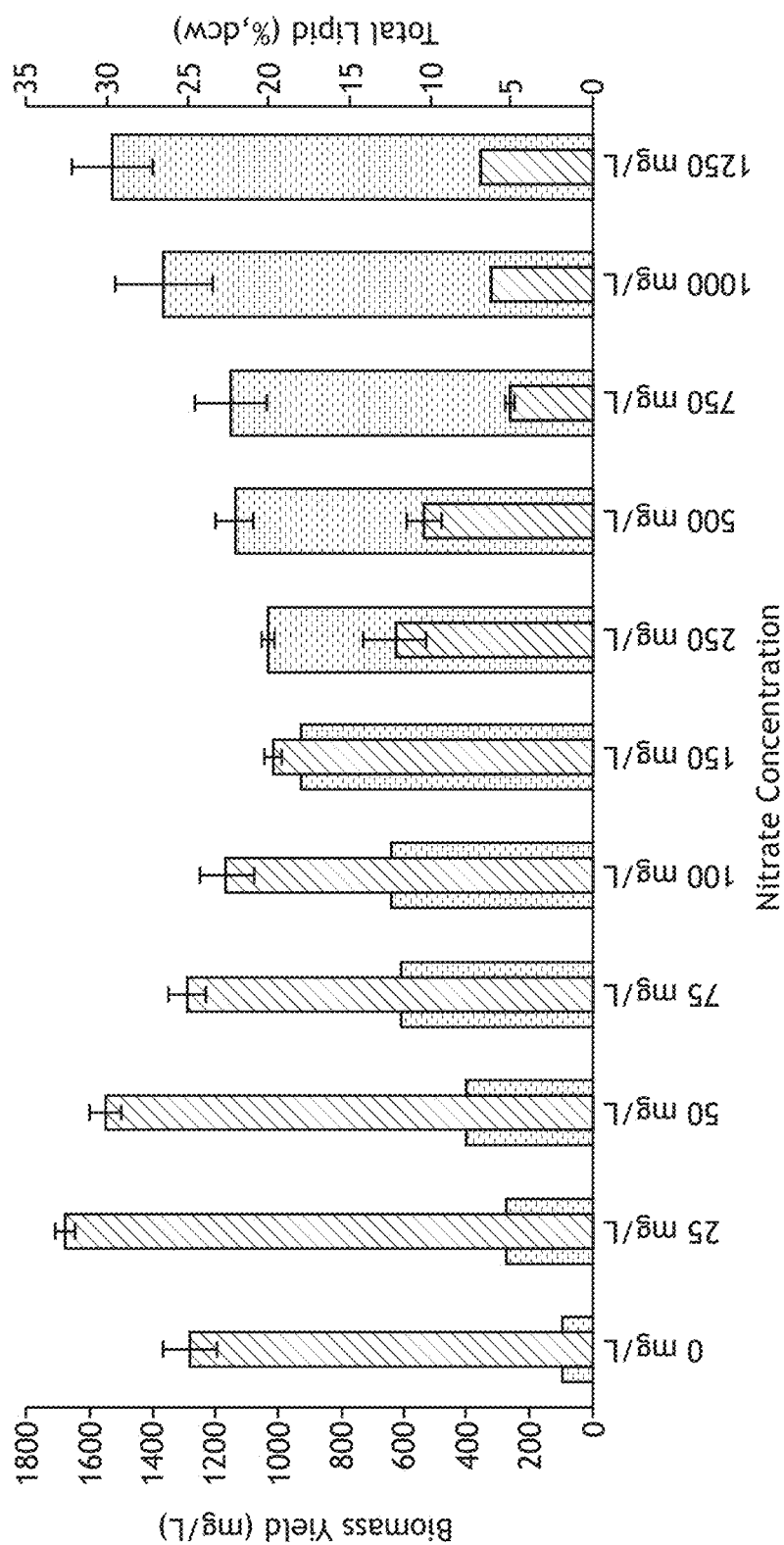
FIG. 6 is a graph illustrating biomass yield and total lipid yield in different concentrations of nitrate from an algal photobioreactor system after 14 days, in accordance with one or more embodiments of the present disclosure.

FIG. 6 is a graph illustrating biomass yield and total lipid yields using different concentrations of nitrate in an algal photobioreactor system 200, in accordance with one or more embodiments of the present disclosure (e.g., dry cell weight (DCW)) using different concentrations of nitrate from a algal photobioreactor system 200 incorporating the method 300 and filter assembly 100 of the present disclosure.) FIG. 6 illustrates the direct relationship between nitrogen-bound nitrate concentrations, growth, and TAG synthesis. Under white light, 1% $CO_2$ and 25° C., there is an optimal relationship between biomass and lipid at an initial concentration of 250 mg/L nitrate after 14 days; at this endpoint nitrate has been depleted to less than 10 mg/L.

Figure 7A:
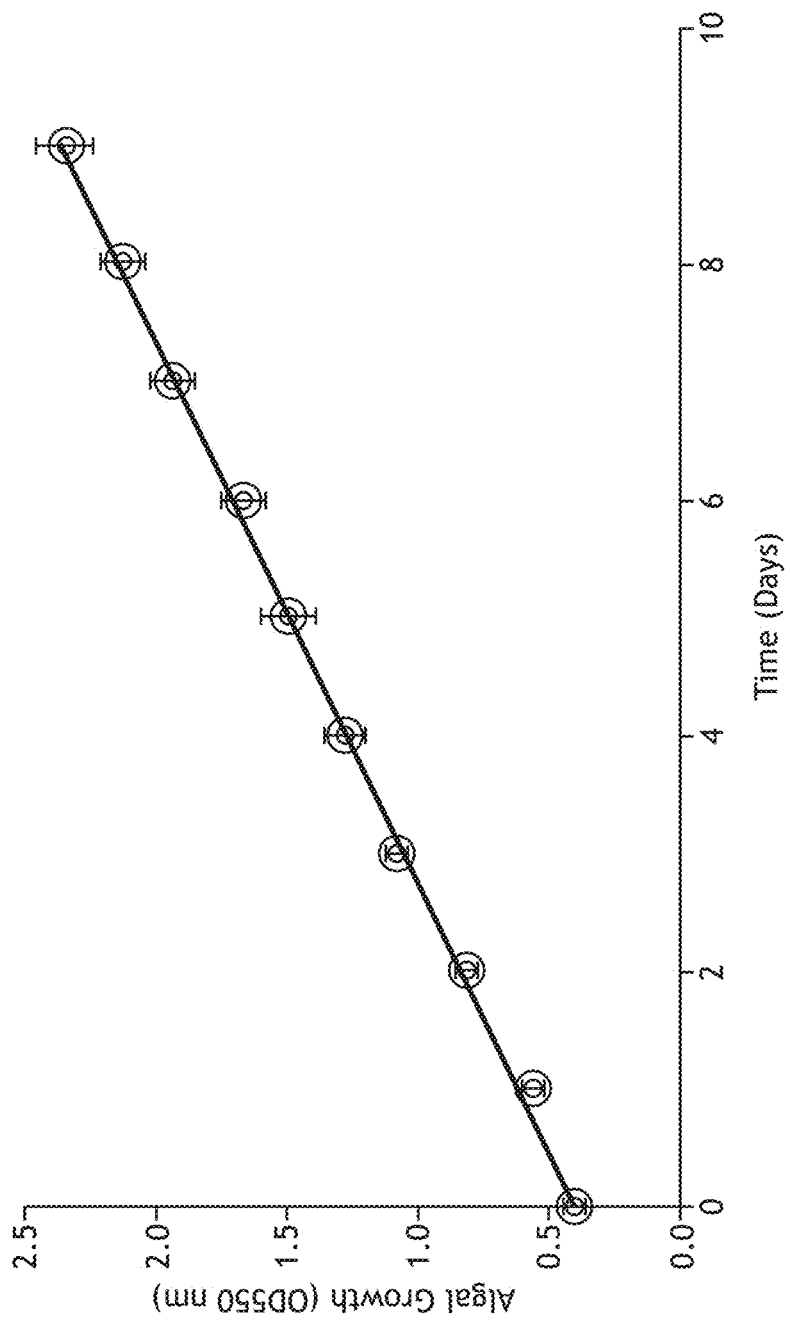
FIG. 7A is a graph illustrating biomass accumulation using *Tetradesmus obliquus* in an algal bioreactor system using optimal lighting conditions, in accordance with one or more embodiments of the present disclosure.
Figure 7B:
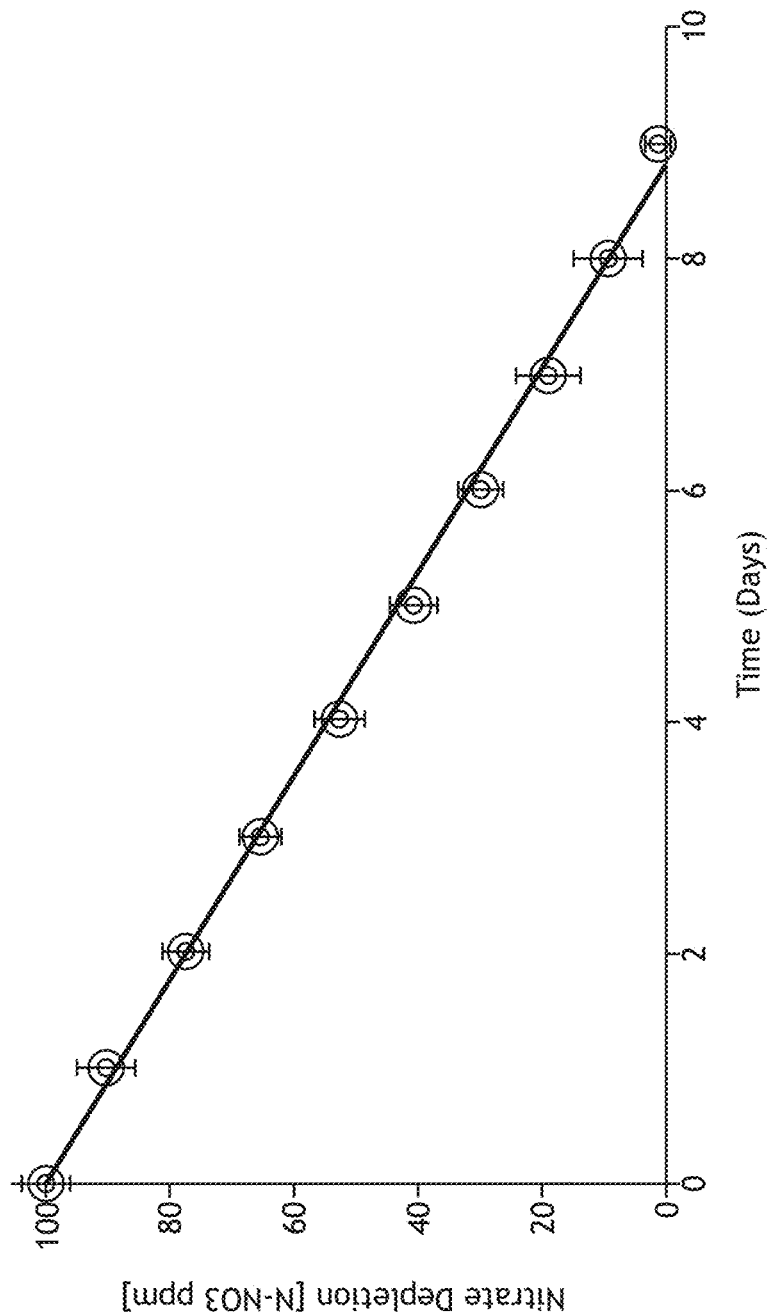
FIG. 7B is a graph showing depletion of nitrogen-bound nitrate in an algal photobioreactor system using *Tetradesmus obliquus* in Bold's Basal Medium under optimal lighting conditions, in accordance with one or more embodiments of the present disclosure.

FIG. 7A is a graph illustrating biomass accumulation in an algal photobioreactor system using *Tetradesmus obliquus* coincident with the depletion nitrogen-bound nitrate using 250 mg/L nitrogen-bound nitrate in defined media. A combination of red and blue light was the most effective in supporting growth (at 800 μmol/m²/sec in the presence of 1% $CO_2$, 100 mg/L nitrate, 25° C.). Concentrations of nitrogen-bound nitrate considerably reduced under these conditions (e.g., as shown in FIG. 7B).

Figure 8:
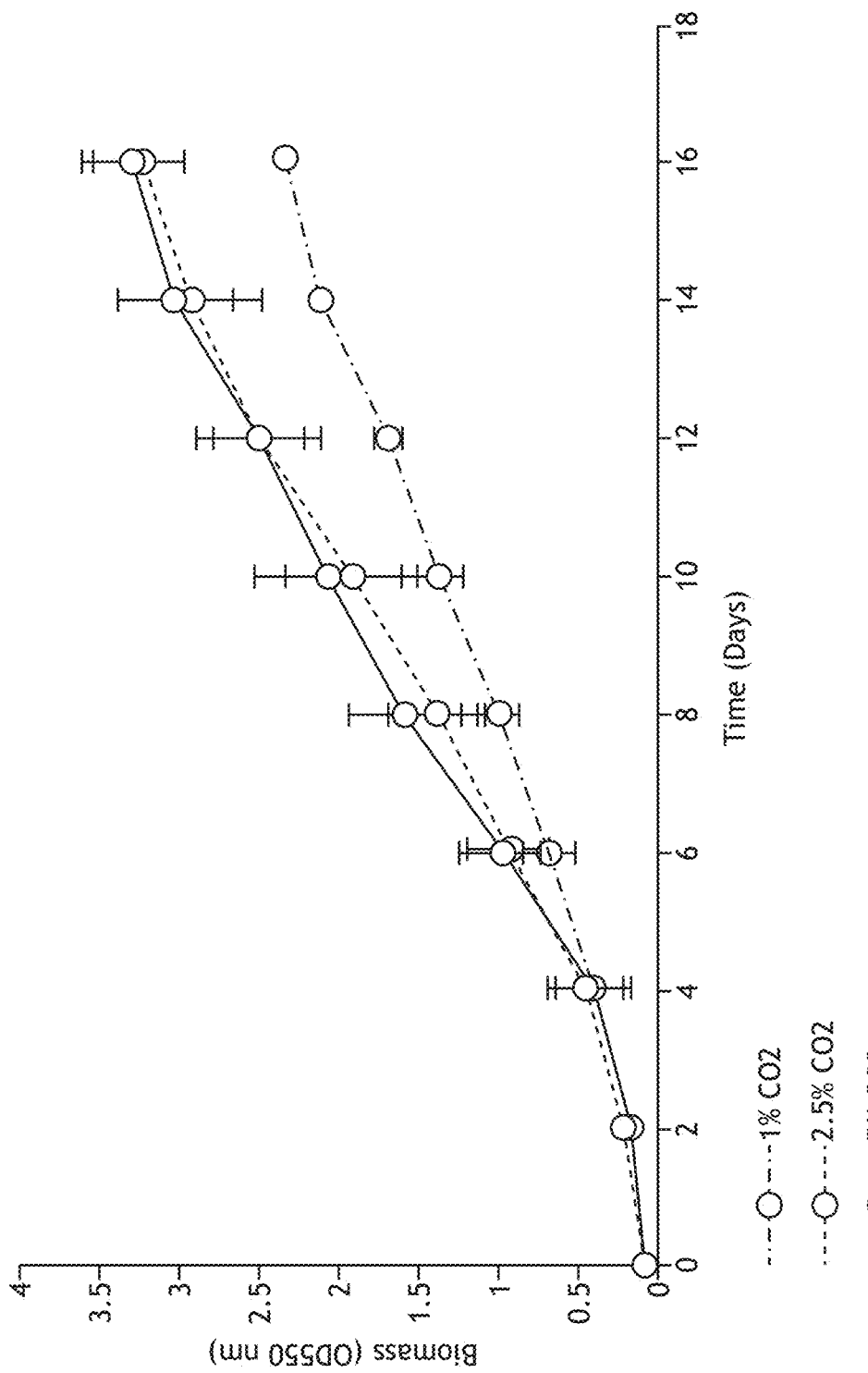
FIG. 8 is a graph illustrating biomass production at different $CO_2$ levels, in accordance with one or more embodiments of the present disclosure.

FIG. 8 is a graph illustrating biomass production at different $CO_2$ levels. Using 250 mg/L nitrogen-bound nitrate in defined media, optimal growth conditions in the presence of $CO_2$ at 25° C. were defined. As shown in FIG. 8, growth at 2.5% and 5% $CO_2$ were indistinguishable and ~30% higher that growth in the presence of 1% $CO_2$. Under all three concentrations of $CO_2$, nitrate levels were reduced to less than 10 mg/L by day 8.

With the established growth conditions described above (150 mg/L nitrate, red-blue light at 500 μmol/m²/sec, 2.5% CO2 at 25° C.), several yield parameters were determined. Total biomass yield is greater than 100 mg dry weight algae/L/day, resulting in greater than 1,200 mg/L of 12 days; for a 200 L system. The biomass productivity per day (logarithmic growth of the unicellular algae) was 72.9 mg/L/day (±6.2). The unicellular algae doubled every 2.13 days (±0.21). The percent lipid content of the biomass was 28.5% (±0.5). The percent TAG percentage was 18.7% (±4.5).

Figure 9:
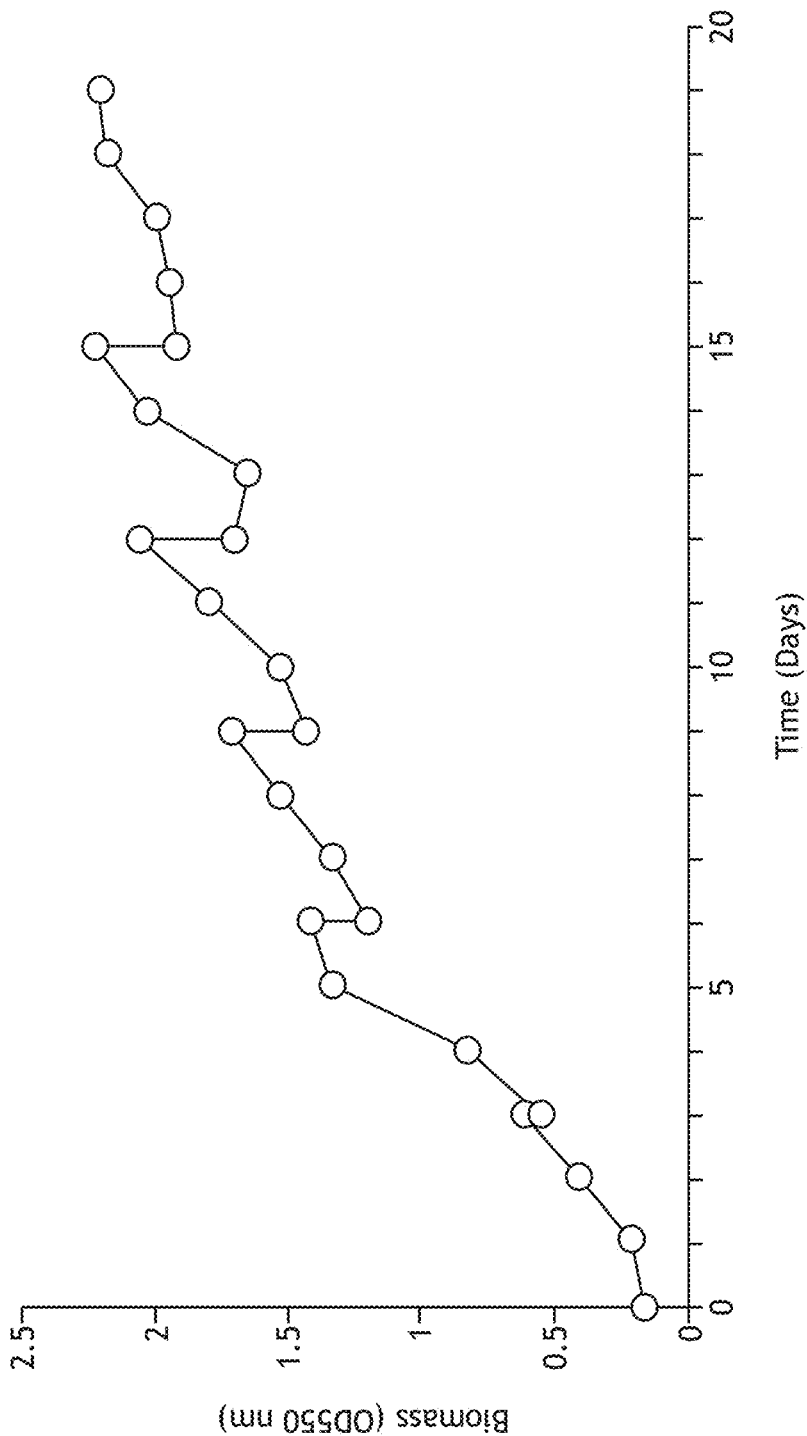
FIG. 9 is a graph illustrating the time (in days) it takes to accumulate biomass using secondary wastewater from a municipal water system in an algal photobioreactor system, in accordance with one or more embodiments of the present disclosure.

FIG. 9 is a graph illustrating the time (in days) required for biomass to accumulate using waste water in an algal photobioreactor system (white light at 500 μmol/m²/sec, 1% $CO_2$, 25° C.) resulting in both high biomass and oil production. Nitrogen-bound nitrate concentrations in wastewater ranged from 20-100 mg/L. To maintain nitrogen-bound nitrate levels to support growth, 10% v/v of secondary wastewater was added every 3 days. Maximal biomass is achieved at 18 days. The cyclic drop in density indicates the addition of secondary wastewater (10% v/v)).

Using wastewater under the algal photobioreactor system noted in FIG. 6, total lipid increases to 35% (algal dry weight) at day 15 were measured with a total oil content of 27% (algal dry weight).

It is to be understood that embodiments of the methods disclosed herein may include one or more of the steps described herein. Further, such steps may be carried out in any desired order and two or more of the steps may be carried out simultaneously with one another. Two or more of the steps disclosed herein may be combined in a single step, and in another embodiment, one or more of the steps may be carried out as two or more sub-steps. Further, other steps or sub-steps may be carried in addition to, or as substitutes to one or more of the steps disclosed herein.

The present disclosure has been illustrated in detail with reference to specific examples. It is to be noted that the examples should not be interpreted as a limitation of the present disclosure, but merely as an illustration.

The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

What is claimed:

1. A filtration assembly comprising:
   a filter plate containing at least one pore;
   a filter column attached to an algal photobioreactor system and configured to receive at least one species of unicellular alga grown in the algal photobioreactor system; and
   at least one species of filamentous alga disposed within the filter column, wherein the at least one species of filamentous alga is grown onto to the filter plate and acts as a stationary phase within the filter column and collects the at least one species of unicellular alga.

2. The filtration assembly of claim 1, wherein the at least one species of filamentous alga comprises: a single celled alga that forms a structure of at least one of long chains, threads, filaments, or pseudofilaments.

3. The filtration assembly of claim 1, wherein the at least one species of filamentous alga comprises: at least one of *Bumilleriopsis filiformis*, *Tribonema aequale*, *Tribonema affine*, *Tribonema minus*, or *Tribonema viride*.

4. The filtration assembly of claim 1, wherein the at least one species of filamentous algae binds with the at least one species of unicellular cell alga through electrostatic processes.

5. The filtration assembly of claim 1, wherein a diameter of the at least one pore ranges from 0.25 μm to 5 μm.

6. An algal photobioreactor system comprising:
   a photobioreactor chamber;
   a reservoir;
   a filtration assembly;
   a unicellular alga; and
   a light source, wherein the filtration assembly comprises:
      a filter plate containing at least one pore;
      a filter column attached configured to receive at least one species of unicellular alga grown in the algal photobioreactor system; and
      at least one species of filamentous alga disposed within the filter column, wherein the at least one species of filamentous alga is grown onto to the filter plate and acts as a stationary phase within the filter column and collects the at least one species of unicellular alga.

7. The algal photobioreactor system of claim 6, wherein the at least one species of filamentous alga comprises:
at least one of *Bumilleriopsis filiformis, Tribonema aequale, Tribonema affine, Tribonema minus,* or *Tribonema viride*.

8. The algal photobioreactor system of claim 6, wherein the at least one species of unicellular alga comprises:
at least one of *Coccomyxa subellipsoidea* or *Tetradesmus obliquus*.

9. A method of removing nitrogen-bound nitrate from at least one of ground water, surface water, or waste water comprising:
providing contaminant-containing water from at least one of groundwater, surface water, or waste water sources;
adding the contaminant-containing water to an algal photobioreactor system;
adding an algal culture to the algal photobioreactor system;
adjusting at least one of temperature, $CO_2$ concentration, pH, light wavelength, or light intensity in the algal photobioreactor system to enhance growth of algae;
removing water from the algal culture; and
harvesting algal biomass, wherein the algal photobiorector system comprises:
a photobioreactor chamber;
a reservoir;
a filtration assembly;
a unicellular alga; and
a light source, wherein the filtration assembly comprises:
a filter plate containing at least one pore;
a filter column attached to the algal photobioreactor system for growth of at least one species of unicellular alga; and
at least one species of filamentous alga disposed within the filter column, wherein the at least one species of filamentous alga is grown onto to the filter plate and acts as a stationary phase within the filter column and collects the at least one species of unicellular alga.

10. The method of claim 9, further comprising the step of extracting at least one of lipids, proteins, or carbohydrates from the algal biomass.

11. The method of claim 9, further comprising the step of adjusting at least one of the temperature, the $CO_2$ concentration, the pH, the light wavelength, or the light intensity in the algal photobioreactor system to enhance lipid synthesis.

12. The method of claim 11, wherein 20% to 35% of a dry weight of the algal biomass contains lipids.

13. The method of claim 11, wherein 35% to 40% of a dry weight of the algal biomass contains lipids.

14. An algal biomass with high lipid content prepared by a process comprising:
providing water from at least one of groundwater, surface water, or waste water source;
adding the water to an algal photobioreactor system;
adding an algal culture to the algal photobioreactor system;
adjusting at least one of temperature, $CO_2$ concentration, pH, light wavelength, or light intensity in the algal photobioreactor system to enhance triglyceride production;
removing water from the algal culture;
harvesting the algal biomass, wherein the algal photobiorector system comprises:
a photobioreactor chamber;
a reservoir;
a filtration assembly;
a unicellular alga; and
a light source, wherein the filtration assembly comprises:
a filter plate containing at least one pore;
a filter column attached to the algal photobioreactor system for growth of at least one species of unicellular alga; and
at least one species of filamentous alga disposed within the filter column, wherein the at least one species of filamentous alga is grown onto to the filter plate and acts as a stationary phase within the filter column and collects the at least one species of unicellular alga.

15. The algal biomass with a high lipid content prepared by a process of claim 14, wherein the water from the at least one of groundwater, surface water, or waste water source contains greater than 10 ppm nitrogen-bound nitrate.

16. The algal biomass with a high lipid content prepared by a process of claim 14, wherein 20% to 35% of a dry weight of the algal biomass contains lipids.

17. The algal biomass with a high lipid content prepared by a process of claim 14, wherein 35% to 40% of a dry weight of the algal biomass contains lipids.

* * * * *